(12) United States Patent
Emmons

(10) Patent No.: US 6,733,480 B2
(45) Date of Patent: May 11, 2004

(54) DECLOGGING MULTILUMEN DISCHARGE ASSEMBLY

(75) Inventor: Clifford L. Emmons, Oakville, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 149 days.

(21) Appl. No.: 10/099,808

(22) Filed: Mar. 14, 2002

(65) Prior Publication Data

US 2002/0156435 A1 Oct. 24, 2002

Related U.S. Application Data

(60) Provisional application No. 60/189,846, filed on Mar. 16, 2000.

(51) Int. Cl.[7] .............................................. A61M 5/32
(52) U.S. Cl. ...................................................... 604/266
(58) Field of Search ........................... 604/27, 244, 264, 604/267, 266, 275, 248, 533, 539

(56) References Cited

U.S. PATENT DOCUMENTS 4,978,336 A 12/1990 Capozzi et al.
5,116,315 A 5/1992 Capozzi et al.

Primary Examiner—Michael J. Hayes
Assistant Examiner—Michael M Thompson

(57) ABSTRACT

A multilumen discharge assembly for delivering mixed biological adhesives is provided, which comprises a base portion including a flow path to provide mixed biological adhesives therethrough, and an elongate cylinder defining a plurality of axially extending flow channels connected to an outlet port, where the elongate cylinder is rotatably mounted relative to the base portion to permit sequential alignment of said flow path with a respective one of said plurality of flow channels upon rotation thereof. The discharge assembly further includes a declogging mechanism disposed adjacent the elongate cylinder and including at least one scraping member for scraping a portion of said outlet port to provide a substantially clear opening for delivering mixed biological adhesives. The declogging mechanism may include a declogging projection to eject clogging material from the opening in said outlet port and/or at least one scraper to remove clogging material from peripheral portions around the outlet port upon rotation of the elongate cylinder.

13 Claims, 3 Drawing Sheets

DECLOGGING MULTILUMEN DISCHARGE ASSEMBLY

CROSS REFERENCE TO RELATED APPLICATIONS

This application claims priority to U.S. Provisional application entitled "Declogging Multilumen Discharge Assembly" filed on Mar. 16, 2000 and assigned Serial No. 60/189,846.

BACKGROUND

1. Technical Field

The present disclosure related generally to a biological and/or synthetic fluid delivery system and, more particularly, to a longitudinally extending multilumen discharge assembly for dispensing mixed components of biologically compatible tissue adhesives, synthetic sealants and/or hemostats.

2. Description of Related Art

Biologically derived as well as synthetic sealants, hemostats and/or adhesives are used to treat wounds in instances where external dressings or sutures are not totally effective.

A common treatment takes advantage of the rapid reaction which occurs when a solution of clotting factors, such as fibrinogen, comes into contact with a solution of a catalyst, such as thrombin, to form a complex which acts as a tissue adhesive. This rapid reaction typically commences within 2 second after the solutions initially contact one another, and it typically attains a soft set within 10 second of contact. A common name for such a complex is fibrin glue.

Prior fibrin glue delivery systems may generally be categorized as utilizing either turbulence within a solution or overlapping contact of airborne sprays to obtain mixing. The apparatus utilized by either of these systems typically includes confining a fibrinogen solution separately from a thrombin solution, then permitting these two solutions to mix either immediately prior to or upon application on a wound. Typically, these solutions are confined within separate syringes prior to mixing. An example of a delivery system based on internal mixing of two solutions is provided in U.S. Pat. Nos. 4,978,336 and 5,116,315, both to Capozzi et al., the content of which are incorporated herein by reference.

SUMMARY

The present invention is directed to a declogging multilumen discharge assembly for applying biological adhesives to a surgical site. The discharge assembly comprises an elongate cylinder having a plurality of axially extending flow channels for delivery of mixed biological adhesives, and a declogging mechanism is disposed within or adjacent the elongate cylinder for providing a clear opening for the delivery in case clogging is detected within the flow channel currently in use. In a preferred embodiment, the elongate cylinder is rotatably mounted to a base portion of the discharge assembly to permit sequential alignment of the plurality of flow channels with a flow path disposed at the base portion for providing a new or unused flow channel when the one flow channel currently in use is determined to be improper for further use because of clogging therein.

BRIEF DESCRIPTION OF THE DRAWINGS

Preferred embodiments of the disclosure are described herein with reference to the drawings, wherein.

DETAILED DESCRIPTION OF PREFERRED EMBODIMENTS

The preferred embodiments of declogging multilumen discharge assembly for endoscopic or laparoscopic surgical use are disclosed herein.

Figure 1:
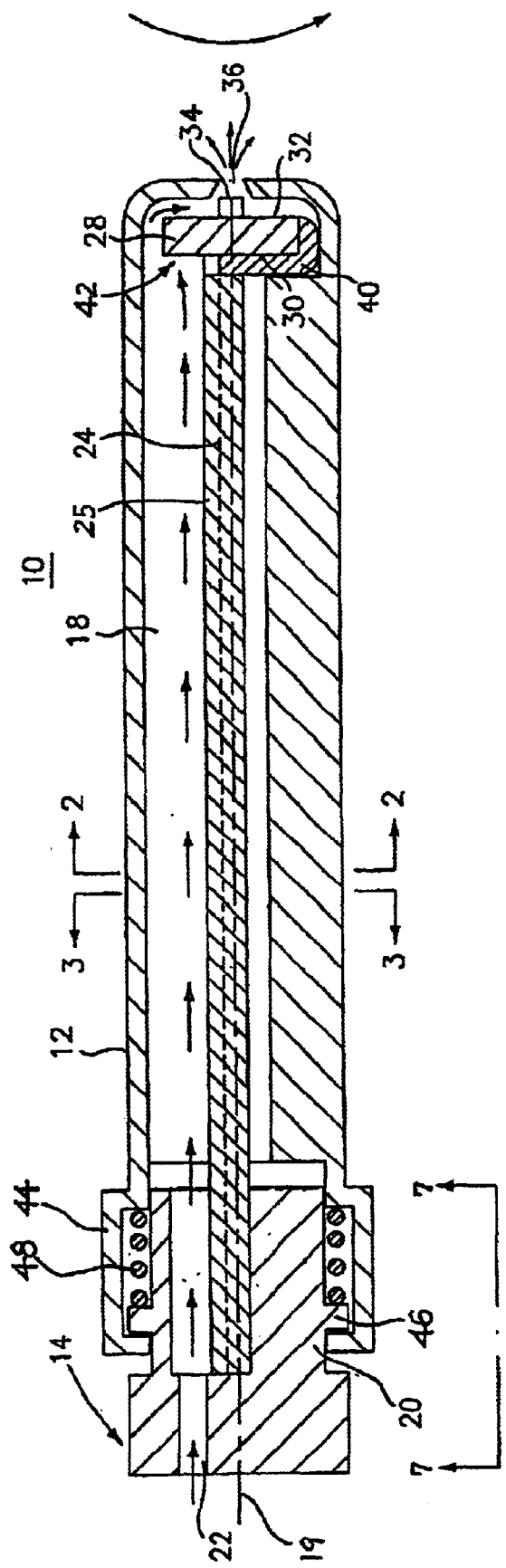
FIG. 1 is a side cross-sectional view of a declogging multilumen discharge assembly, illustrating a base portion, an elongate cylinder and a declogging mechanism in accordance with one embodiment of the present invention.
Figure 2:
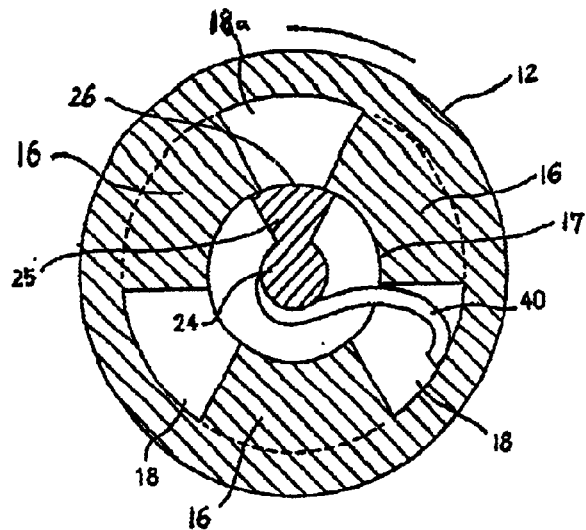
FIG. 2 is a cross-sectional distal view of the declogging multilumen discharge assembly of FIG. 1, illustrating a plurality of flow channels of the elongate cylinder and the declogging mechanism disposed at a distal portion thereof, which is taken along the line 2—2 in FIG. 1.
Figure 3:
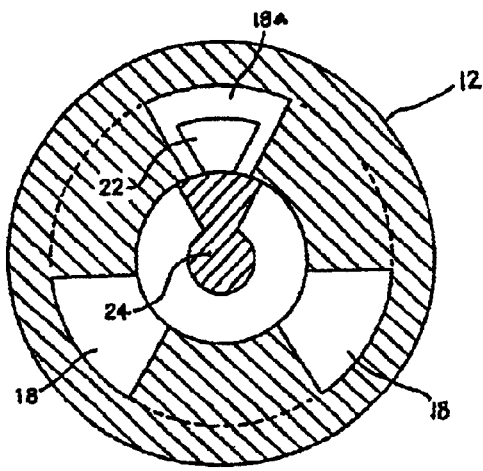
FIG. 3 is a cross-sectional proximal view of the multilumen discharge assembly of FIG. 1, illustrating proximal portions of the elongate cylinder and base portion, which is taken along the line 3—3 in FIG. 1.

Referring to FIGS. 1–3, in a preferred embodiment, a declogging multilumen discharge assembly referenced generally as 10 is illustrated. The multilumen discharge assembly 10 includes an elongate cylinder 12 and a base portion 14.

The base portion 14 of the discharge assembly 10 is configured and dimensioned to attach to a manifold assembly or adhesive supply system (not shown) having at least a two component biological adhesive contained therein. The base portion 14 is designed to receive thoroughly mixed biological adhesive through a flow path 22 and to convey the mixed biological adhesive to an outlet port 36 located at the distal end of the elongate cylinder 12.

The elongate cylinder 12 includes a plurality of flow channels 18 extending longitudinally therethrough to convey the mixed biological adhesive. In a preferred embodiment, as best seen in FIGS. 2 and 3, the elongate cylinder 12 includes a plurality of wall portions 16 which extend radially toward the center portion of the elongate cylinder 12 and define circular faces 17 with a radius from the center line 19. An elongate shaft 24 is mounted to the base portion 14 and defines the center line 19 of the discharge assembly 10. The elongate shaft 24 includes a radially extended portion 25 defining a circular outer face 26 with the same radius as the circular faces 17 in order to establish an enclosed channel 18a among the multiple flow channels 18.

The elongate cylinder 12 is rotatably mounted relative to a mounting collar 20 of the base portion 14 in order to sequentially align the flow path 22 in the base portion 14 with a respective one of the flow channels 18. In operation, when one flow channel is substantially clogged with hardened or hardening biological adhesive, the user can change to a new or unused flow channel by rotating the elongated cylinder 12 relative to the base portion 14, thereby aligning the new flow channel with the flow path 22 of the base portion. The alignment structure is best illustrated in FIG. 3.

Figure 4:
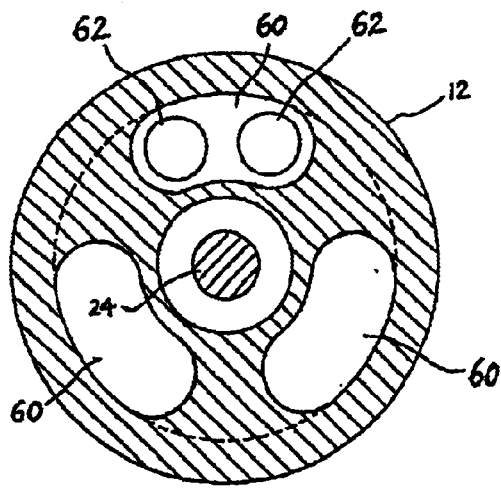
FIG. 4 is a cross-sectional view similar to FIG. 3, illustrating an alternate structure of elongate cylinder and base portion.

Referring to FIG. 4, as an alternative embodiment, the elongate shaft 24 may not include a radially extending portion 25 as in FIG. 2, and the elongate cylinder 12 has a plurality of enclosed flow channels 60 of generally circular cross section, axially extending along the elongate cylinder 12. Here, the plurality of flow channels 60 define enclosed flow channels by themselves without the cooperation of the portion 25 as in FIG. 2. Instead of having one flow path, the base portion 14 may have two separate flow paths 62 for conveying adhesive components separately therethrough, which are adapted in direct fluid communication with the respective one of flow channels 60.

Figure 5:
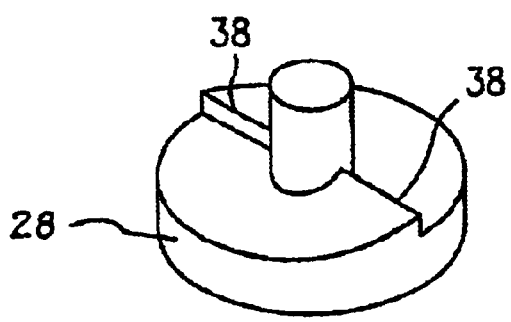
FIG. 5 is a perspective view illustrating a scraper and a declogging projection of the declogging mechanism in accordance with the preferred embodiment of FIG. 1.

Referring back to FIGS. 1–3, elongate shaft 24 extends from base portion 14 to adjacent the distal end portion of the elongate cylinder 12. The shaft 24 includes a disk 28 having a proximal surface 30 and a distal surface 32. A declogging projection 34 extends distally from the distal surface 32 in axial alignment with an outlet port or atomizing opening 36. In addition, at least one scraper 38 with a scraping edge is formed on the distal surface 32 (best seen in FIG. 5) extending distally therefrom. As seen in FIGS. 1 and 2, a declogging arm 40 is positioned adjacent the disk 28. Both the scraper 38 and the declogging arm 40 are configured to remove clogging material from a distal cavity 42 or adjacent the outlet port 36 of the discharge assembly upon rotation of elongate cylinder 12.

In addition to permitting rotational movement as described above, the elongate cylinder 12 is also telescopically collapsible relative to the mounting collar 20 (FIG. 1). In a preferred embodiment, elongate cylinder 12 includes an enlarged portion 44 to receive mounting collar 20 of the base portion 14. The mounting collar 20 includes a flange 46 to receive a spring 48 between the mounting collar 20 and enlarged portion 44. The spring 48 is biased to push the elongate cylinder 12 to a normal position as seen in FIG. 1.

In operation, discharge assembly 10 is mounted to a known manifold structure (not shown) configured to convey multiple biological components. Mixed biological adhesive is delivered from the manifold to a flow channel 18 through a flow path 22. The mixed biological adhesive is conveyed distally to the atomizing opening or outlet port 36 in the distal end of elongate cylinder 12. Alternatively, as described above with FIG. 4, the base portion 14 may have two separate flow paths 62 in fluid communication with the one flow channel 60. In this case, two adhesive components are separately delivered from the manifold to a proximal portion of the flow channel 60 through their respective flow paths. Mixing occurs through the flow channel 60, and mixed adhesive is conveyed to the outlet port 36.

Figure 6:
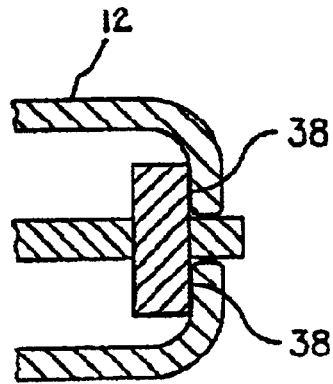
FIG. 6 is a side cross-sectional view of the distal end portion of the discharge assembly in accordance with the embodiment, illustrating the declogging projection positioned to eject clogging material from the outlet port of the elongate cylinder.
Figure 7:
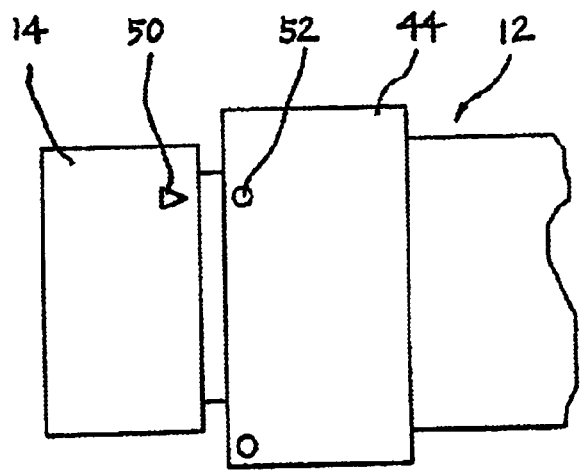
FIG. 7 is a side elevational view of the proximal end portion of the discharge assembly in accordance with one embodiment, illustrating alignment markings in the base portion and elongate cylinder, which is taken along the line 7—7 in FIG. 1.

Over time, if the biological material hardens and clogs, the flow channels 18 or 60 and/or outlet port 36, elongate cylinder 12 is simply rotated to align another clean flow channel 18 or 60 with regard to the flow path(s) 22 or 62 in the base portion 14. In order to facilitate alignment, alignment markings 50, 52 are provided at the base portion 14 and proximal portion of the elongate cylinder 12. (See FIG. 7.) In addition to rotating elongate cylinder 12, proximal pressure is applied to drive declogging projection 34 into atomizing opening or outlet port 36 to clear the opening for its next use. Also, applying proximal pressure on elongate cylinder 12 during rotation causes scrapers 38 to clear clogging material from the peripheral portions around outlet port 36. (See FIG. 6.) At the same time, declogging arm 40 serves to remove clogging material from the distal portion of the flow path 18 on rotation of cylinder 12.

It is envisioned that the structure and configurations of the elongate cylinder, base portion, elongate shaft may be varied. Any commercially suitable material known in the art can be used to form the multilumen discharge assembly including the elongate shaft and base portion as described in various embodiments herein above. It is also envisioned that the multilumen, elongate shaft may be formed from transparent material to monitor clogging therein.

While the above description contains many specifics, these specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A multilumen discharge assembly for delivering mixed biological adhesives comprising:
    a base portion including a flow path to provide mixed biological adhesives there-through;
    an elongate cylinder defining a plurality of axially extending flow channels connected to an outlet port, said elongate cylinder rotatably mounted relative to said base portion to permit sequential alignment of said flow path with a respective one of said plurality of flow channels upon rotation thereof wherein said elongate cylinder is adapted to provide longitudinal movement of at least a distal portion thereof to eject at least a portion of said clogging material; and
    a declogging mechanism disposed adjacent said elongate cylinder and including at least one scraping member for scraping a portion of said outlet port to provide a substantially clear opening for delivering mixed biological adhesives wherein said declogging mechanism further includes a declogging projection disposed at a distal end of a longitudinally extending shaft in axial alignment with said opening in said outlet port to eject clogging material from said opening.

2. A multilumen discharge assembly as in claim 1 wherein said declogging mechanism further includes a declogging projection to eject clogging material from said opening in said outlet port.

3. A multilumen discharge assembly as in claim 1 wherein said declogging mechanism includes a longitudinally extending shaft extending from said base portion to adjacent a distal end of said elongate cylinder, and said at least one scraping member is disposed at a distal end of said longitudinally extending shaft.

4. A multilumen discharge assembly as in claim 3 wherein said at least one scraping member is adapted for scraping peripheral portions around said outer port upon rotation of said elongate cylinder.

5. A multilumen discharge assembly as in claim 4 wherein said at least one scraping member includes at least one scraper for scraping adjacent a distal end surface of said elongate cylinder and at least one declogging arm for scraping an inner circumferential portion there around.

6. A multilumen discharge assembly as in claim 4 wherein said plurality of axially extending flow channels merge in an open space adjacent said distal end of said elongate cylinder for receiving said declogging mechanism therein.

7. A multilumen discharge assembly as in claim 1 further including an indicator for indicating said sequential alignment.

8. A multilumen discharge assembly as in claim 1 wherein said elongate cylinder is formed from transparent material to monitor clogging therein.

9. A multilumen discharge assembly for delivering mixed biological adhesives comprising:
- a base portion including a plurality of flow paths to separately provide adhesive components therethrough;
- an elongate cylinder defining a plurality of axially extending flow channels connected to an outlet port, said elongate cylinder rotatably mounted relative to said base portion to permit sequential alignment of said plurality of flow paths with a respective one of said plurality of flow channels upon rotation thereof; and
- a declogging mechanism disposed adjacent said elongate cylinder and including at least one scraping member to provide a substantially clear opening for delivering mixed biological adhesives.

10. A multilumen discharge assembly as in claim 9 wherein said declogging mechanism includes a declogging projection to eject clogging material from an outlet opening of said outlet port.

11. A multilumen discharge assembly as in claim 9 wherein said at least one scraping member is configured to scrape peripheral portions around said outlet port upon rotation of said elongate cylinder.

12. A multilumen discharge assembly as in claim 9 wherein said at least one scraping member is configured to scrape around inner circumferential portions adjacent a distal end of said elongate cylinder.

13. A multilumen discharge assembly as in claim 9 wherein said elongate cylinder is formed from transparent material to monitor clogging therein.

* * * * *